(12) United States Patent
Wu (10) Patent No.: US 11,872,121 B2
(45) Date of Patent: Jan. 16, 2024

(54) PUSH AND TWIST MECHANISM FOR INTERFACING A DRIVE MECHANISM HANDPIECE WITH AN INTRAOCULAR LENS CARTRIDGE

(71) Applicant: Alcon Inc., Fribourg (CH)

(72) Inventor: Yinghui Wu, Cedar Hill, TX (US)

(73) Assignee: Alcon Inc., Fribourg (CH)

( * ) Notice: Subject to any disclaimer, the term of this patent is extended or adjusted under 35 U.S.C. 154(b) by 458 days.

(21) Appl. No.: 16/999,394

(22) Filed: Aug. 21, 2020

(65) Prior Publication Data

US 2021/0052370 A1 Feb. 25, 2021

Related U.S. Application Data

(60) Provisional application No. 63/023,389, filed on May 12, 2020, provisional application No. 62/890,859, filed on Aug. 23, 2019.

(51) Int. Cl.
*A61F 2/16* (2006.01)

(52) U.S. Cl.
CPC ............ *A61F 2/1678* (2013.01); *A61F 2/167* (2013.01); *A61F 2/1667* (2013.01)

(58) Field of Classification Search
CPC ...... A61F 2/1678; A61F 2/1667; A61F 2/167; A61F 2/1672; A61F 2/1664; A61F 2/1662
See application file for complete search history.

(56) References Cited

U.S. PATENT DOCUMENTS

| | | | |
|---|---|---|---|
| 8,647,382 B2 | 2/2014 | Kudo et al. |
| 9,314,373 B2 | 4/2016 | Kudo |
| 9,421,092 B2 | 8/2016 | Brown |
| 2004/0059343 A1 | 3/2004 | Shearer et al. |
| 2010/0305577 A1 | 12/2010 | Muchhala |
| 2019/0224002 A1 | 7/2019 | Springer |

*Primary Examiner* — Robert A Lynch
(74) *Attorney, Agent, or Firm* — Patterson + Sheridan, LLP (57) ABSTRACT

Systems, methods, and apparatuses for inserting an intraocular lens (IOL) into an eye, are provided. An apparatus comprises an IOL cartridge comprising a nozzle, a compartment, and a plunger case. The nozzle is in fluid communication with the compartment, and the plunger case is in fluid communication with the compartment. The plunger is disposed within the plunger case. The plunger case is configured to removably attach to a handpiece.

17 Claims, 8 Drawing Sheets

PUSH AND TWIST MECHANISM FOR INTERFACING A DRIVE MECHANISM HANDPIECE WITH AN INTRAOCULAR LENS CARTRIDGE

CROSS-REFERENCE TO RELATED APPLICATIONS

This application claims priority to and benefit of U.S. Provisional Patent Application No. 62/890,859, filed Aug. 23, 2019, and U.S. Provisional Patent Application No. 63/023,389, filed May 12, 2020. The entire contents of these applications are incorporated by reference herein in their entirety.

TECHNICAL FIELD

The present disclosure generally relates to eye surgery and, more particularly, some embodiments may generally relate to systems, methods, and apparatuses for removably attaching a drive mechanism handpiece to an intraocular lens (IOL) cartridge.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery.

For cataract surgery, a surgical procedure may require incisions and insertion of tools within an eye to replace the clouded lens with an IOL. An insertion tool can be used for delivery of the IOL into the eye. By way of example, the insertion tool may include a plunger for forcing the IOL out of the nozzle of the insertion tool. In some instances, the IOL may be preloaded in the insertion tool. In other instances, a separate bay may be loaded into the insertion tool. The plunger may engage the IOL to advance the IOL from the bay, through a nozzle, and into the eye.

SUMMARY

In an exemplary embodiment, the present disclosure provides an apparatus for delivery of an IOL. The apparatus may comprise an IOL cartridge comprising a nozzle, a compartment, a plunger, and a plunger case. The compartment may be configured to receive the IOL. The compartment may be in fluid communication with the nozzle, and the plunger case may be in fluid communication with the compartment. The plunger case may be configured to removably attach to a handpiece. The plunger may be disposed within the plunger case.

In another exemplary embodiment, the present disclosure provides an apparatus, for delivery of an IOL. The apparatus may comprise a handpiece comprising a housing and a push rod disposed within the housing. A distal end of the push rod may be configured to removably attach to an IOL cartridge.

In another exemplary embodiment, the present disclosure provides a method for delivery of an IOL into an eye. The method may comprise inserting an IOL cartridge into a housing of a handpiece. The IOL cartridge may further comprise a nozzle, a plunger, a plunger case, and a compartment. The compartment may further comprise the IOL and an IOL folding mechanism. The nozzle may be in fluid communication with the compartment. The plunger case may be in fluid communication with the compartment. The plunger may be disposed within the plunger case. The method may further comprise inserting a distal end of a push rod of the handpiece into a passage of the plunger; rotating the handpiece to lock the IOL cartridge to the handpiece; and rotating the push rod to unlock the plunger from its lock-constrain and lock the push rod to the plunger.

In another exemplary embodiment, the present disclosure provides an apparatus for delivering an IOL. The apparatus may comprise an IOL cartridge comprising a compartment for receiving an IOL, a plunger case having a distal end coupled to the compartment and a proximal end, and a plunger disposed within the plunger case. The apparatus may further comprise a handpiece configured to be removably coupled to the proximal end of the plunger case and comprising a housing and a push rod disposed within the housing and configured to releasably couple to the plunger of the plunger case.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments of the present disclosure provide a variety of preloaded IOL cartridge designs. These preloaded cartridges may be used with handpieces that include different types of drive mechanisms. Particular embodiments of the present disclosure allow interchangeability between different handpieces such as disposable and reusable handpieces, and various preloaded IOL cartridge designs. The disposable handpieces may include non-powered drive mechanisms that are not electrically powered. The reusable handpieces may include non-powered drive mechanisms (e.g., simply manual pushing or screwing, manually actuated via a fluid or a resilient member such as a spring) as well as electrically powered drive mechanisms (e.g., stator windings). It should be noted that these types of handpieces are examples and that other types of handpieces or drive mechanisms may be utilized in accordance with particular embodiments of the present disclosure.

Particular embodiments of the present disclosure include a standard interface mechanism that employs a push and twist functionality for assembling the handpiece with the preloaded IOL cartridge, delivering the IOL, and disengaging the handpiece from the used cartridge if needed. The standard interface allows the different types of handpieces to be easily paired to and utilized with the preloaded IOL cartridges for IOL implantation. After IOL implantation, the preloaded IOL cartridges can be easily detached from the reusable handpieces.

The handpiece may be secured to the preloaded IOL cartridge by sliding an end of the handpiece over the plunger case of the IOL cartridge. In certain embodiments, the end of the handpiece may have one or more slots for engaging with a pin or protrusion on the IOL cartridge. The handpiece may be rotated approximately 90 degrees clockwise, for example, to lock the protrusion of the IOL cartridge in place in the slot of the handpiece.

The IOL cartridge may further include a locking cap positioned on an end of the plunger case. The locking cap may be engaged with one end of the plunger. The locking cap can be turned 90 degrees, for example, in order to unlock the plunger and release the plunger from its shipping and storing position within the IOL cartridge.

A push rod of the drive mechanism can then be rotated from a disengaged position to be engaged with the plunger of the IOL cartridge in order to advance the plunger. In some embodiments, the push rod may be rotated an amount between 60 degrees and 120 degrees of rotation, or in some particular embodiments, approximately 90 degrees, in order to be engaged with the plunger. The push rod can be disengaged from the plunger by rotating, for example, 90 degrees, in the opposite direction. Once the IOL delivery has been completed, the handpiece may be rotated and pulled apart from the used IOL cartridge.

Figure 1:
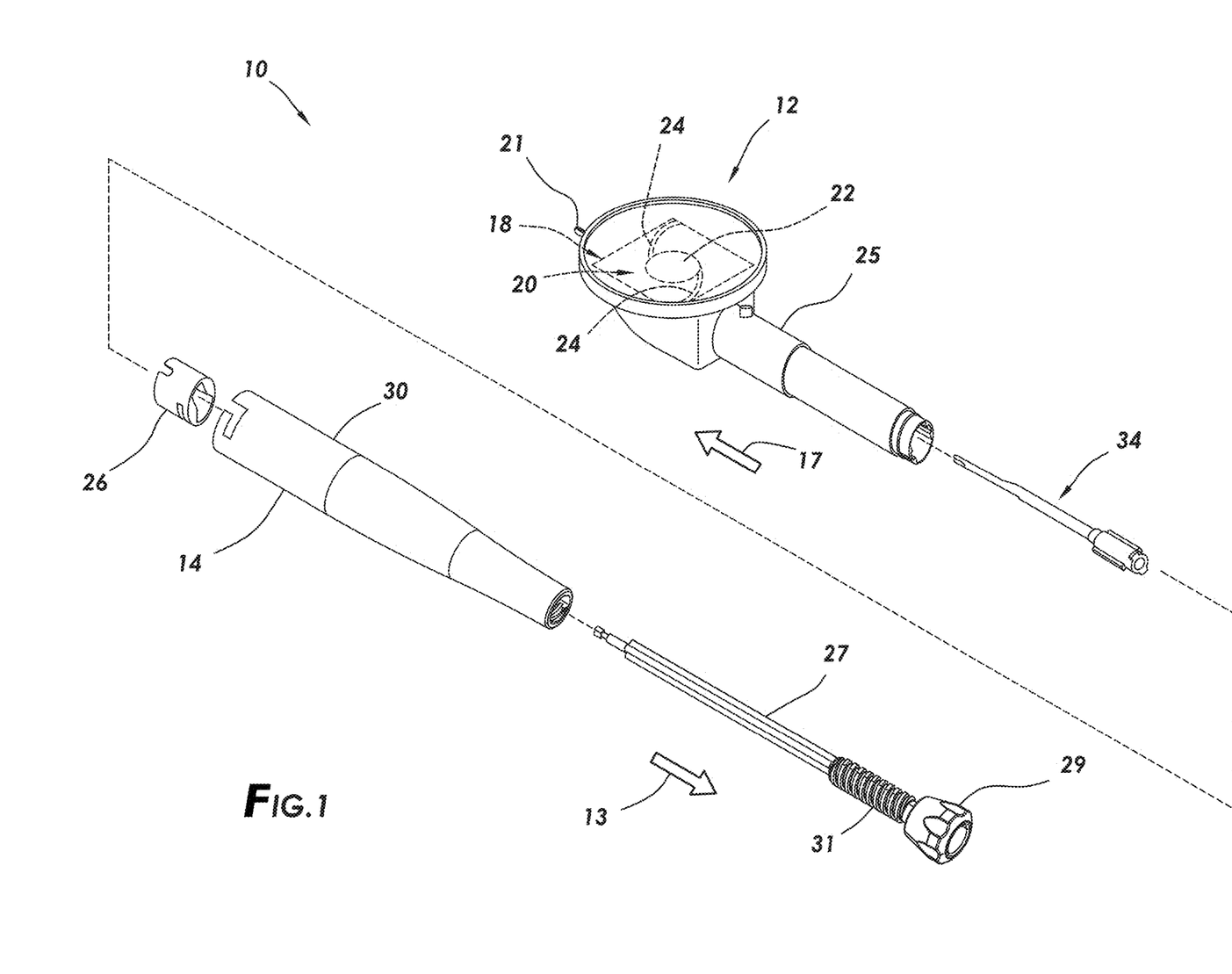
FIG. 1 illustrates an exploded view of an insertion tool, in accordance with some embodiments of the present disclosure.

FIG. 1 illustrates an exploded view of an insertion tool 10 for implanting an IOL 20, in accordance with particular embodiments of the present disclosure. As illustrated, the insertion tool 10 may include an IOL cartridge 12 and a handpiece 14. The IOL cartridge 12 and the handpiece 14 may be removably attached to one another.

The IOL cartridge 12 may include a compartment 18 containing an IOL 20. In operation, the handpiece 14 may be actuated to advance the IOL 20 from the IOL cartridge 12. The IOL 20 may include a lens 22 and haptic extensions 24. The haptic extensions 24 may be side struts (or other suitable extensions) extending from the lens 22 that may stabilize the IOL 20 when it may be disposed within the patient's eye. It should be understood that the IOL 20 is merely exemplary and that techniques disclosed herein may be used with any suitable IOL. For example, a modular IOL (not shown) that includes a lens portion disposable in a base with haptic extensions may also be used. The IOL cartridge 12 may also include a nozzle 21 that is in fluid communication with the compartment 18. The IOL cartridge 12 may include a folding mechanism (not shown) to fold the IOL 20. For example, the IOL cartridge 12 may include calipers or arms (not shown) to fold the IOL 20 for delivery into an eye. The IOL cartridge 12 may also include a plunger case 25. The plunger case 25 may be a hollow and rigid member that removably attaches to the handpiece 14. The plunger case 25 of the IOL cartridge 12 may be inserted into the handpiece 14, and the handpiece 14 may be rotated to engage with the plunger case 25. A locking cap 26 may be disposed on an end of the plunger case 25. A plunger 34 may be movably disposed within the plunger case 25. The plunger 34 may be an elongated rigid member made of plastic and may be used for delivering the IOL 20.

The handpiece 14 may be removably attached to the IOL cartridge 12. It should be noted that various handpieces may be used with different types of IOL cartridges. The handpiece 14 may include an electrically powered or a non-electrically powered drive mechanism that may include a push rod 27 extending along a length of the handpiece 14. The push rod 27 may be movably disposed within a housing 30 of the handpiece 14 and may be manually actuated via a rotatable dial 29, which may cooperate with a fluid or a resilient member such as a spring 31 or another actuation mechanism. In general, for the purposes of discussing and describing the various components and features of the handpiece 14 and the IOL cartridge 12 of the IOL insertion tool 10, reference to a proximal end or direction may refer to a direction more towards an end of the handpiece 14 comprising the rotatable dial 29, according to directional arrow 13. Likewise, reference to a distal end or direction may refer to a direction more towards an end of the IOL cartridge 12 comprising the nozzle 21, according to directional arrow 17.

Figure 2:
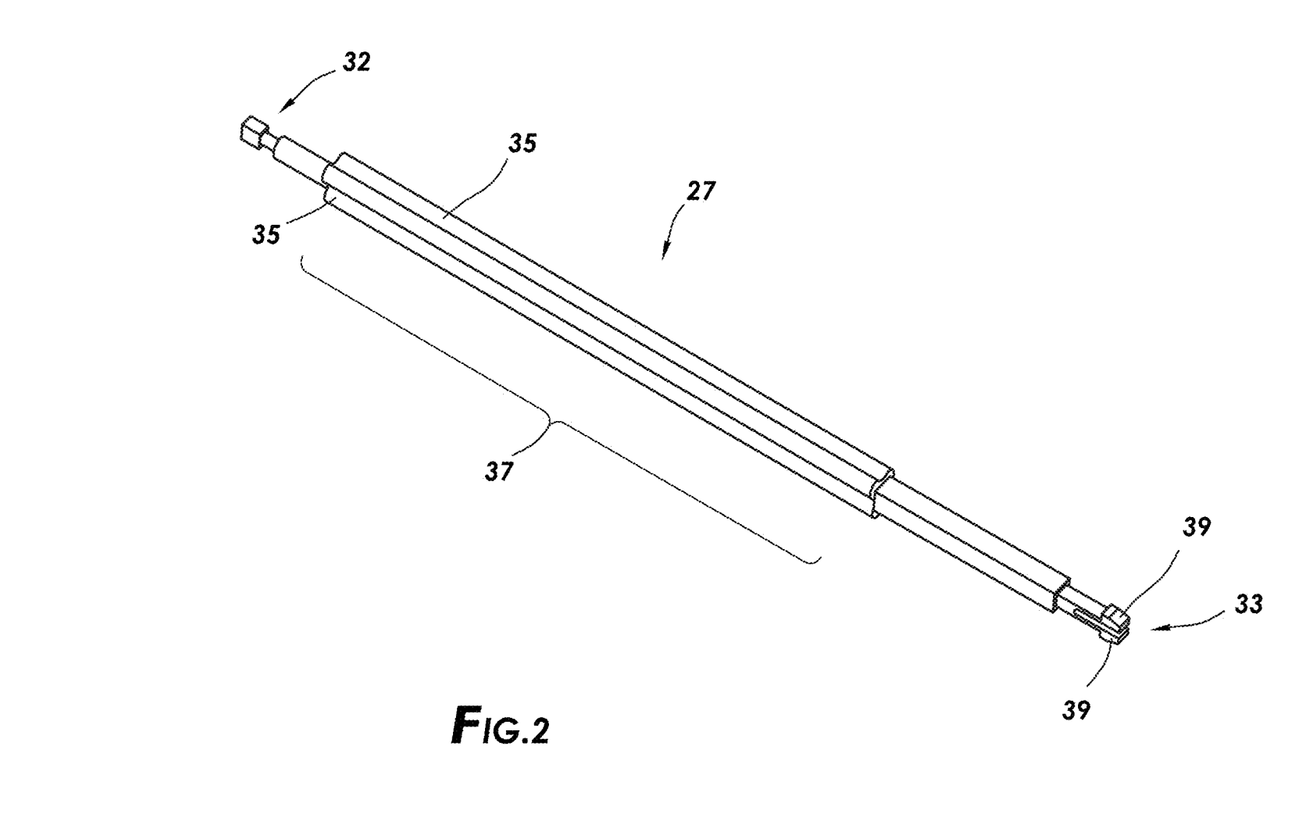
FIG. 2 illustrates a top perspective view of a push rod, in accordance with some embodiments of the present disclosure.

FIG. 2 illustrates the push rod 27 in accordance with particular embodiments of the present disclosure. The push rod 27 may be an elongated rigid member that includes a distal end 32 opposite to a proximal end 33. The push rod 27 may be made of various materials such as plastic and/or rubber, for example. The push rod 27 may include elongated ridges 35 along a middle portion 37. A height of the middle portion 37 may be greater than heights of the distal end 32 and the proximal end 33. The distal end 32 may include a shape of a quadrilateral, for example. However, other suitable shapes can be utilized. The proximal end 33 may include members 39 for attachment to the dial 29 (shown on FIG. 1).

Figure 3:
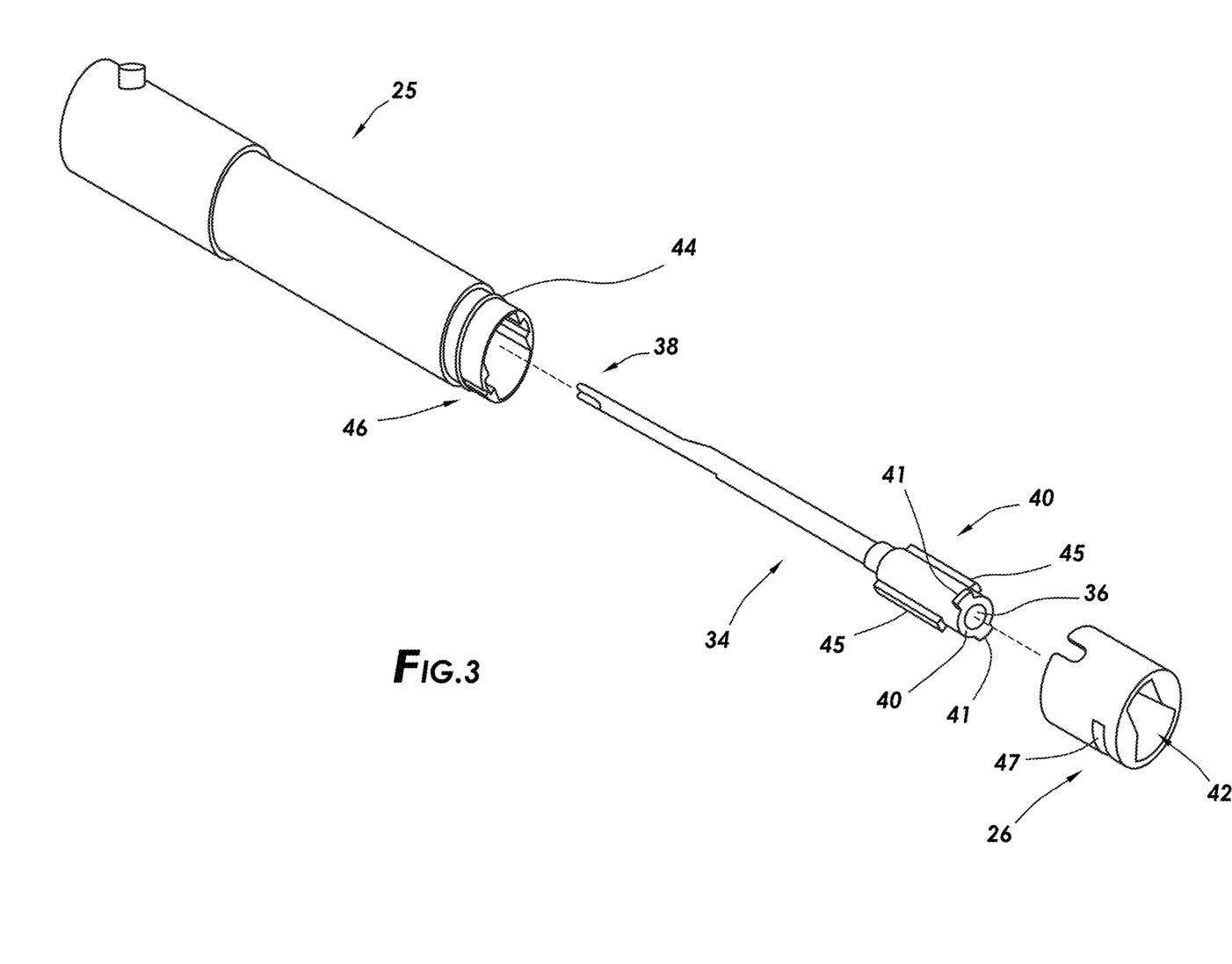
FIG. 3 illustrates an exploded view of a plunger, plunger case, and locking cap of the insertion tool of FIG. 1, in accordance with some embodiments of the present disclosure.

FIG. 3 illustrates the plunger 34 along with the plunger case 25 and the locking cap 26, in accordance with particular embodiments of the present disclosure. The plunger 34 may be movably disposed within the plunger case 25. The plunger 34 may be an elongated rigid member made of plastic and may be used for delivering the IOL 20 (shown on FIG. 1). The plunger 34 may include a passage 36 extending longitudinally through an engagement portion 40 of the plunger 34. The engagement portion 40 may be positioned opposite to a plunger tip 38. The passage 36 may be configured to receive the distal end 32 of the push rod 27 (shown on FIG. 2). Tabs 41 may be positioned on the engagement portion 40. The tabs 41 may extend outward from the engagement portion 40 and are utilized to lock or unlock the plunger 34 within the plunger case 25 via the locking cap 26. The plunger 34 may also include longitudinally extending ridges 45 for stabilization within the plunger case 25.

The locking cap 26 may be configured to engage with the plunger case 25 and the engagement portion 40 of the plunger 34. The locking cap 26 may be of a cylindrical shape and may be configured to prevent axial movement (e.g., forward movement) of the plunger 34 when the locking cap 26 is in a locked position. Additionally, the locking cap 26 may be rotated to an unlocked position to allow axial movement of the plunger 34. The locking cap 26 may include at least one slot 47 for receiving the at least one tab 41 of the plunger 34, for locking or unlocking the plunger 34. The slot 47 may extend along the circumference of the locking cap 26. In a locked configuration, the locking cap 26 may be positioned in a first position such that one or more tabs 41 are placed in the at least one slot 47. To unlock the locking cap 26, the locking cap 26 may be rotated such that the one or more tabs 41 are removed from the slot 47. The locking cap 26 may include a passage 42 to receive the distal end 32 of the push rod 27 (shown on FIG. 2). The locking cap 26 may be press fitted onto a ridge 44 that extends along a circumference of an end 46 of the plunger case 25.

Figure 4:
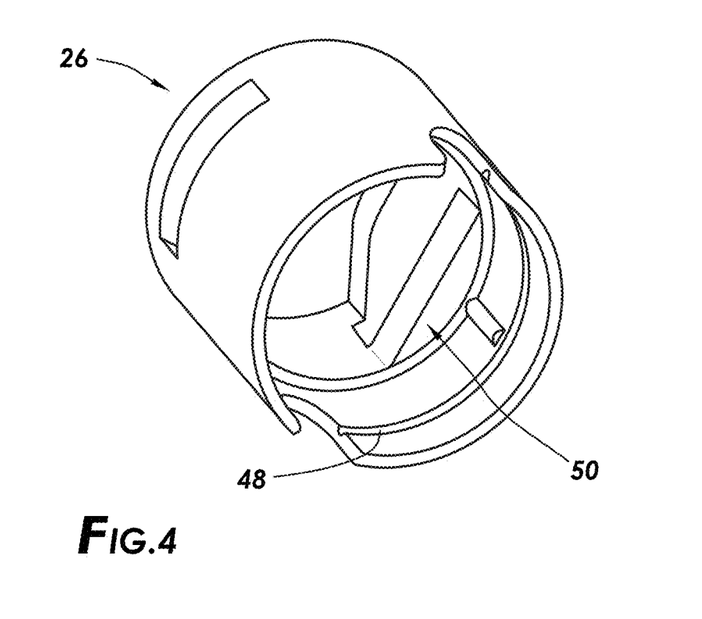
FIG. 4 illustrates an inside perspective view of a locking cap, in accordance with some embodiments of the present disclosure.

FIG. 4 illustrates an inside perspective view of the locking cap 26, in accordance with some embodiments of the present disclosure. An inside of the locking cap 26 may include contoured surfaces 50 to encompass and hold the plunger 34 (shown on FIG. 3) in place, such that there is no lateral movement of the plunger 34. The locking cap 26 also includes an internal groove 48 that extends along an internal circumference of the locking cap 26. The ridge 44 of the plunger case 25 (shown on FIG. 3) may align with the internal groove 48 of the locking cap 26. The ridge 44 in conjunction with the internal groove 48 may allow the locking cap 26 to remain on the end 46 of the plunger case 25 (shown on FIG. 3) and allow the locking cap 26 to rotate or actuate about the end 46 of the plunger case 25.

Figure 5:
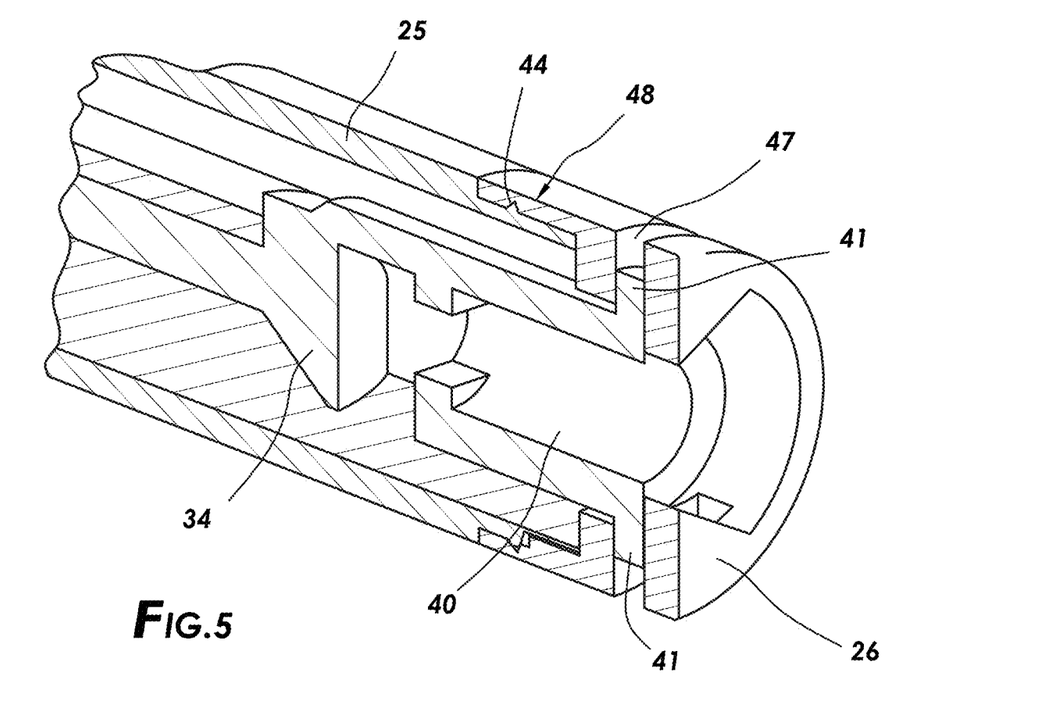
FIG. 5 illustrates a cross-section of a locking cap and a plunger in a locked position within the plunger case, in accordance with some embodiments of the present disclosure.

FIG. 5 illustrates a side view cross-section of the plunger case 25 with the locking cap 26 in an initial position or locked position, in accordance with some embodiments of the present disclosure. The locking cap 26 may be placed on the plunger case 25 to restrict axial movement of the plunger 34. As illustrated, the ridge 44 of the plunger case 25 extends into the internal groove 48 of the locking cap 26 to allow the locking cap 26 to rotate in place. Tabs 41 of the engagement portion 40 of the plunger 34 extend into the slot 47. In this initial position, the plunger 34 is locked to prevent movement during storage or shipping.

Figure 6:
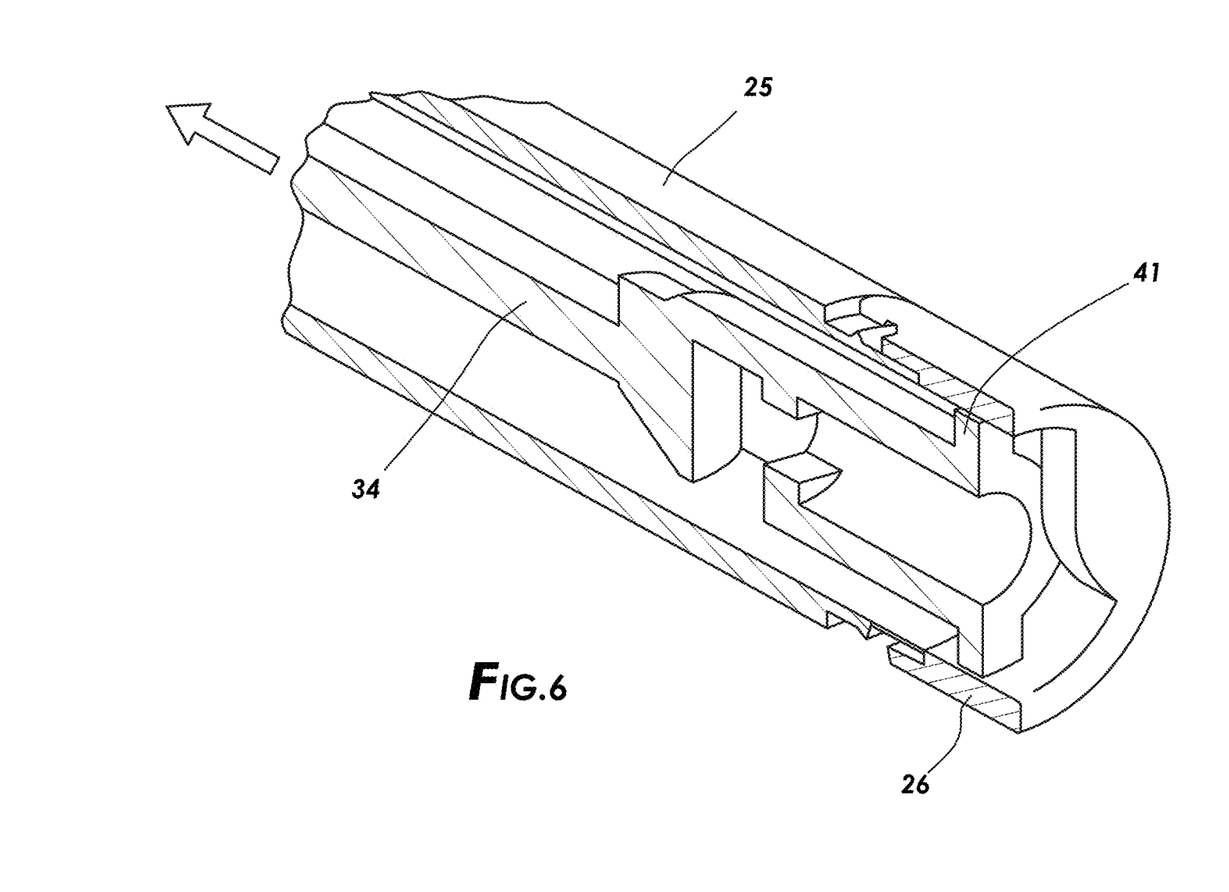
FIG. 6 illustrates a cross-section of a locking cap and a plunger in an unlocked position within the plunger case, in accordance with some embodiments of the present disclosure.

FIG. 6 illustrates a side view cross-section of the plunger case 25 with the locking cap 26 in an unlocked position in accordance with some embodiments of the present disclosure. As illustrated, the locking cap 26 has been rotated to remove or unlock the tabs 41. Once the locking cap 26 is in an unlocked position, the plunger 34 may be axially movable in a forward direction indicated by the arrow.

Figure 7A:
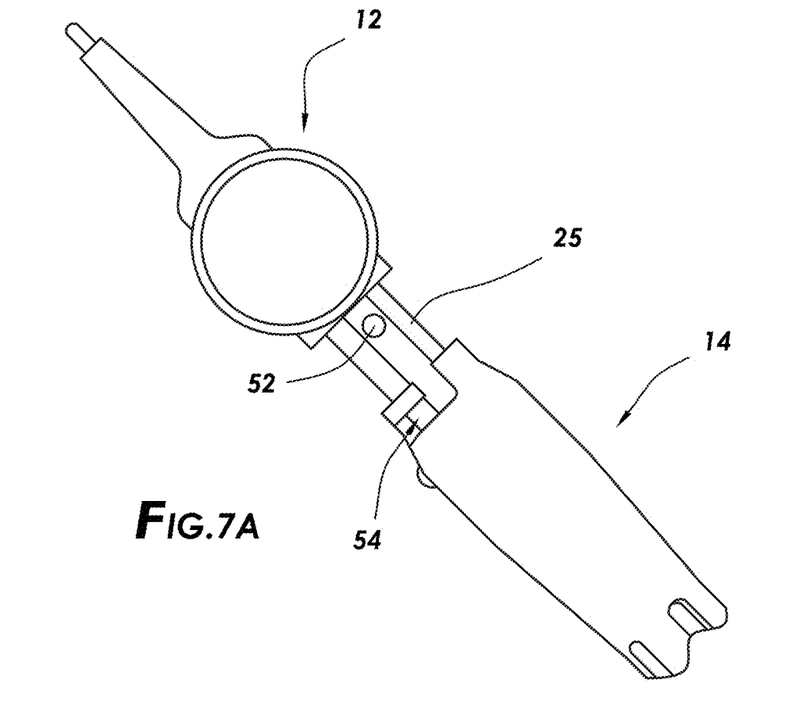
FIG. 7A illustrates inserting the IOL cartridge into the handpiece in accordance with particular embodiments of the present disclosure.

FIG. 7A illustrates inserting the IOL cartridge 12 into the handpiece 14 in accordance with particular embodiments of the present disclosure. The plunger case 25 of the IOL cartridge 12 includes a protrusion 52 that may be aligned with a slot 54 of the handpiece 14. The plunger case 25 is inserted into an inner portion of the handpiece 14 such that the slot 54 receives the protrusion 52. The handpiece 14 may be rotated to secure the IOL cartridge 12 to the handpiece 14. In some embodiments, the handpiece 14 and the IOL cartridge 12 may be configured such that the handpiece 14 is rotated in an amount ranging from 60 degrees to 120 degrees of rotation in order to secure the handpiece 14 to the IOL cartridge 12. For example, in some particular embodiments, the handpiece 14 and the IOL cartridge 12 may be configured for a 90 degree amount of rotation to secure the handpiece 14 to the IOL cartridge 12.

Figure 7B:
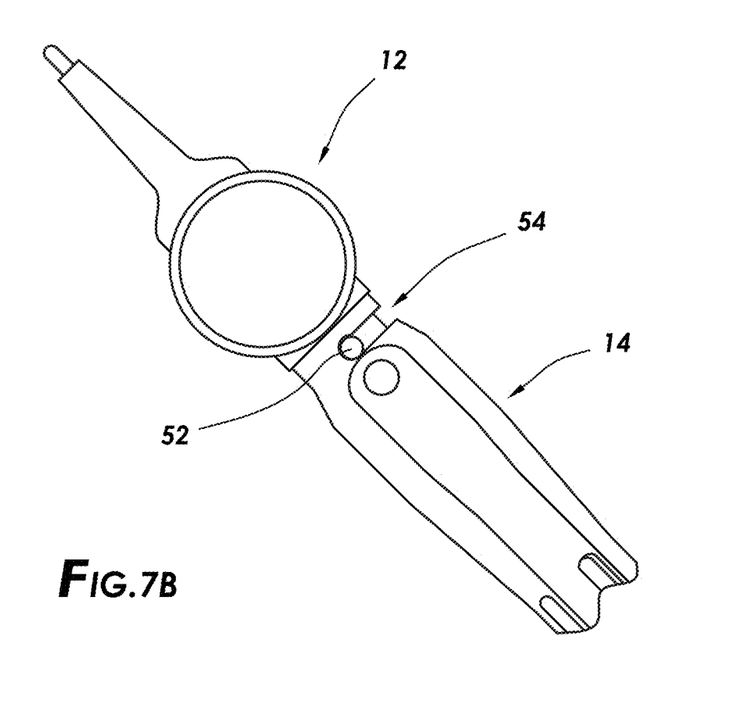
FIG. 7B illustrates the IOL cartridge locked to the handpiece, in accordance with some embodiments of the present disclosure.

FIG. 7B illustrates the IOL cartridge 12 locked to the handpiece 14 in accordance with particular embodiments of the present disclosure. The handpiece 14 has been rotated to secure the protrusion 52 within the slot 54 such that the handpiece 14 and IOL cartridge 12 have been coupled. For unlocking, the handpiece 14 may be rotated in an opposite direction.

Figure 8:
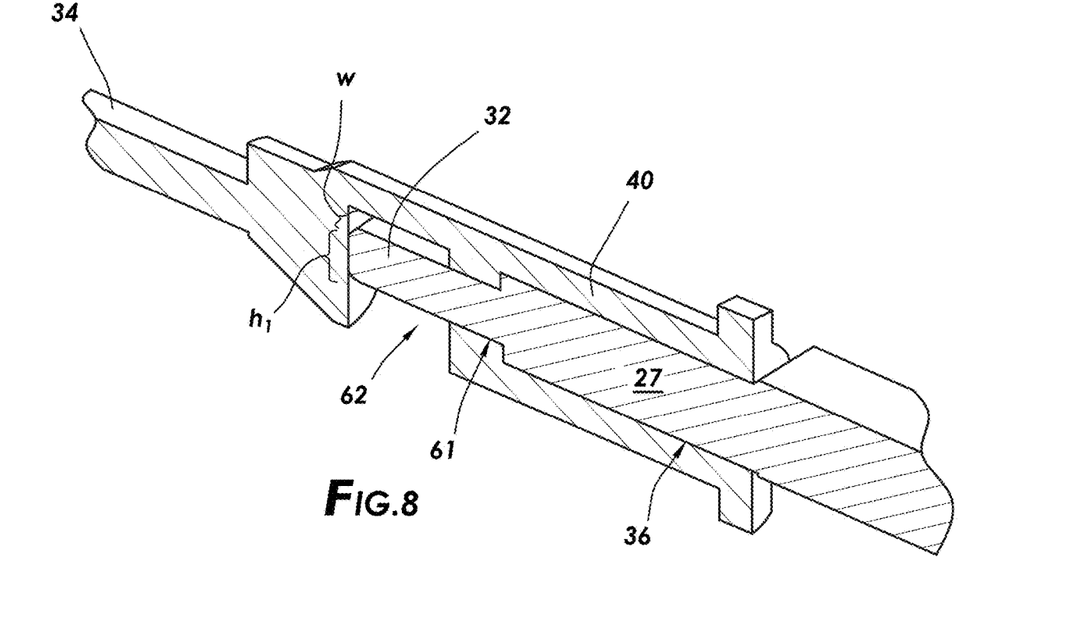
FIG. 8 illustrates a cross-section of a portion of a push rod engaged with a portion of a plunger in an unlocked position, in accordance with some embodiments of the present disclosure.
Figure 9:
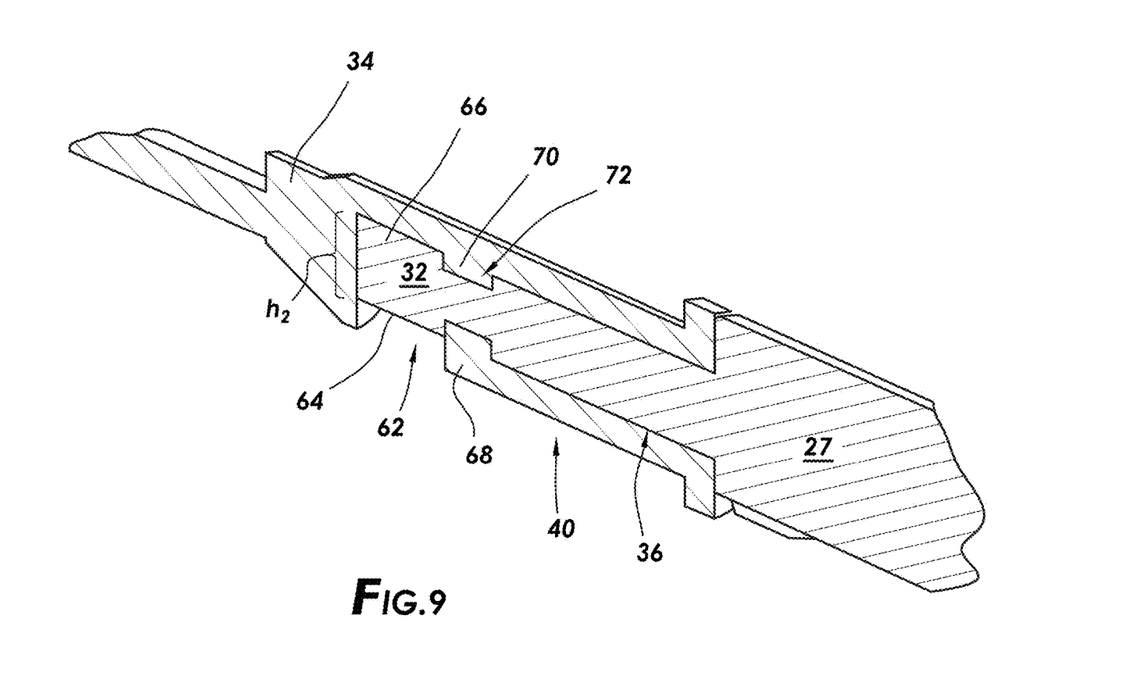
FIG. 9 illustrates a cross-section of a portion of a push rod engaged with a portion of a plunger in a locked position, in accordance with some embodiments of the present disclosure.

FIG. 8 is a cross-section of the distal end 32 of the push rod 27 inserted into the plunger 34, in a non-rotated position or unlocked position, in accordance with particular embodiments of the present disclosure. The passage 36 of the plunger 34 may receive the distal end 32 of the push rod 27. The distal end 32 may include a height $h_1$ in the non-rotated position. The distal end 32 may be of a rectangular shape, for example, which may have a different width (w) and a different height. That is, in a non-rotated position, the distal end 32 has the height, $h_1$, and width, w, and when the distal end 32 is rotated, the width, w, becomes a height $h_2$, as shown in FIG. 9 In some embodiments, $h_2$ may be greater than $h_1$. The passage 36 of the plunger 34 may include a narrow portion 61 that includes an inner diameter that is greater than the height, $h_1$, but less than the width, w, or height $h_2$, thereby allowing the distal end 32 to move through the narrow portion 61 in a non-rotated position (unlocked) but preventing the distal end 32 from passing back through the narrow portion 61 in a rotated position (locked), as shown in FIG. 9. The plunger 34 may include a port 62 that is in fluid communication with the passage 36. The passage 36 of the plunger 34 may be configured to receive the distal end 32 of the push rod 27, and the port 62 may receive a portion of the distal end 32 when the push rod 27 is rotated to a locked position.

FIG. 9 is a cross-section of the distal end 32 of the push rod 27 rotated and locked to the plunger 34 in accordance with particular embodiments of the present disclosure. The distal end 32 is locked into the engagement portion 40 of the passage 36 of the plunger 34. The distal end 32 has been rotated such that a first locking portion 64 and a second locking portion 66 of the distal end 32 abut first internal shoulder 68 and second internal shoulder 70 of the passage 36, thereby locking the push rod 27 to the plunger 34 and preventing axial movement of the push rod 27 relative to the plunger 34. Additionally, the first locking portion 64 may extend into the port 62, when rotated. The height $h_2$ of the distal end 32 may be larger than the inner diameter of a portion 72 of the passage 36 positioned between the first internal shoulder 68 and the second internal shoulder 70 to lock the distal end 32 of the push rod 27 in place and preventing the push rod 27 from being pulled out of the plunger 34.

With reference to FIGS. 1-9, an exemplary technique for assembling the insertion tool 10 in accordance with particular embodiments of the present disclosure is described as follows. In some embodiments, the locking cap 26 of the IOL cartridge 12 may first be rotated from a locked position to an unlocked position, as best shown in FIG. 5 and FIG. 6, respectively. Second, the plunger case 25 of the IOL cartridge 12 may be inserted into the handpiece 14 such that the distal end 32 of the push rod 27 passes through the unlocked locking cap 26 and is received within the passage 36 of the plunger 34, as best shown on FIG. 8. Next, the handpiece 14 may be rotated such that the IOL cartridge 12 is locked to the handpiece 14, as best shown in FIG. 7B. The push rod 27 may be rotated such that the push rod 27 is locked to the plunger 34, as best shown in FIG. 9, to complete the engagement of the handpiece 14 with the IOL cartridge 12 and configure the insertion tool 10 for delivering the IOL 20. In certain embodiments, the push rod 27 may be locked into the plunger 34 before the handpiece 14 is locked to the IOL cartridge 12, or simultaneously when the handpiece 14 is rotated to engage and lock with the IOL cartridge 12. Upon actuation of the push rod 27, the plunger 34 is driven axially forward to move the IOL from the IOL cartridge 12.

To disassemble the insertion tool 10, the push rod 27 may be rotated in an opposite direction, thereby unlocking the push rod 27 from the plunger 34. In some embodiments, this may entail changing the configuration of the push rod 27 and the plunger 34 from the locked configuration of FIG. 9 to the unlocked configuration of FIG. 8. Then, the handpiece 14 may be rotated in an opposite direction, thereby unlocking the IOL cartridge 12 from the handpiece 14. For example, the handpiece 14 may be rotated in a counterclockwise direction from the position shown in FIG. 7B to the position shown in FIG. 7A. In some instances, the counterclockwise rotation may be an amount of rotation in a range of 60 degrees to 120 degrees of rotation, or 90 degrees of counterclockwise rotation in some particular embodiments. In certain embodiments, the handpiece 14 may be unlocked from the IOL cartridge 12 before the push rod 27 is unlocked from the plunger 34, or simultaneously as the push rod 27 is unlocked from the plunger 34. The plunger 34 may then be pulled completely away from the push rod 27 to separate the push rod 27 from the plunger 34 thereby separating the handpiece 14 and the IOL cartridge 12.

Figure 10:
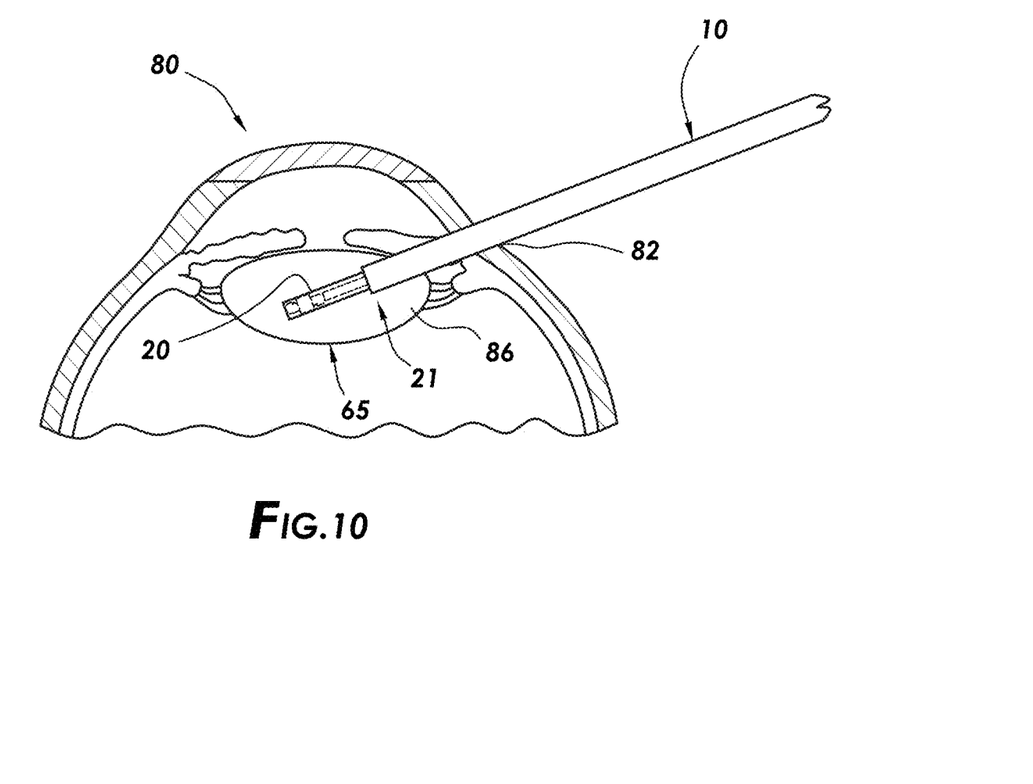
FIGS. 10 and 11 illustrate implantation of an IOL in accordance with some embodiments of the present disclosure.
Figure 11:
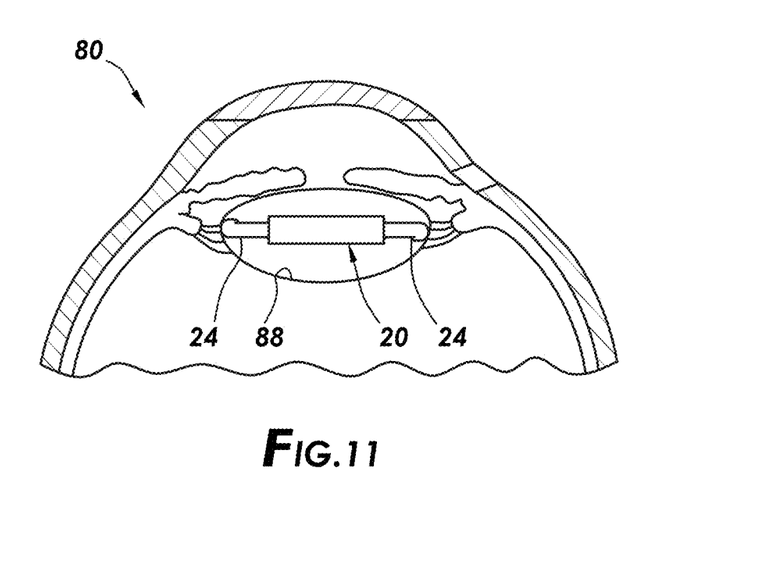

An exemplary technique for implantation of the IOL 20 into an eye 80 of a patient will now be described with respect to FIGS. 10 and 11. As shown on FIG. 10, an incision 82 may be made in the eye 80 by a surgeon. For example, the incision 82 may be made through the sclera of the eye 80. The incision 82 may be a suitable width or length. After the incision 82 is made, the nozzle 21 of the insertion tool 10 may be inserted through the incision 82 into an interior portion 86 of the eye 80. The insertion tool 10 may be actuated to dispense the IOL 20 into a capsular bag 88 of the eye 80.

In some embodiments, the IOL 20 may be delivered in a folded (or rolled configuration) and allowed to unfurl after ejection from the insertion tool 10. Upon dispensation, the IOL 20 should unfurl and settle within the capsular bag 88 of the eye 80, as shown on FIG. 11. The haptic extensions 24 may be manipulated, for example, to engage an equator of the capsular bag 88. The haptic extensions 24 may engage the capsular bag 88 to secure the IOL 20 in the capsular bag 88.

Use of the methods and systems described herein may provide numerous benefits and advantages over other IOL delivery systems. For example, as previously noted, by employing a common or standard interface between IOL cartridges and handpieces including drive mechanisms, interchangeable pairing and utilization of different drive mechanisms and various preloaded IOL cartridge designs may be offered. Thus, a variety of handpieces containing different types of drive mechanisms may be used with each of numerous different types of IOL cartridges, and therefore different types of IOLs. For example, a user may readily select between multiple types of drive mechanism he or she wishes to use depending on the type of IOL and/or the type of IOL cartridge. Additionally, while one user may prefer to use a first type of drive mechanism handpiece for a given IOL cartridge, a different user may have the option of using a second type of drive mechanism handpiece for the same given type of IOL cartridge. Importantly, by allowing for a common, or standard, interface for securing the handpieces to the IOL cartridges, the user experience of securing a handpiece to an IOL cartridge may be substantially the same, regardless of the type of drive mechanism or type of IOL cartridge, and thus IOL, being used, which may also increase ease-of-use for an operator as well as streamline IOL delivery procedures.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:
1. An apparatus for delivery of an intraocular lens (IOL), comprising:
an IOL cartridge comprising:
a nozzle;
a compartment configured to receive the IOL, the compartment in fluid communication with the nozzle; and
a plunger case including a protrusion and a plunger disposed within the plunger case, the plunger case in fluid communication with the compartment, wherein the plunger case is configured to removably attach to a handpiece, the handpiece comprising:
a housing comprising a slot configured to receive the protrusion; and
a push rod disposed within the housing, the push rod comprising a distal end configured to removably attach to the plunger,
wherein:
a portion of the plunger comprises a passage configured to receive the distal end of the push rod;
the push rod is rotatable;

the distal end of the push rod, in a non-rotated position, has a first height, and, in a rotated position, has a second height that is greater than the first height; and a portion of the passage has an inner diameter that is greater than the first height.

2. The apparatus of claim 1, wherein an IOL is disposed within the compartment.

3. The apparatus of claim 1, wherein the inner diameter is less than the second height.

4. The apparatus of claim 3, wherein a rotatable locking cap is disposed on an end of the plunger case.

5. The apparatus of claim 4, wherein the rotatable locking cap comprises a slot configured to receive a tab extending from the portion of the plunger.

6. The apparatus of claim 4, wherein the rotatable locking cap may be rotated to an unlocked position, the unlocked position facilitating an axial movement of the plunger.

7. The apparatus of claim 4, wherein the rotatable locking cap includes at least one slot for receiving at least one tab of the plunger.

8. The apparatus of claim 7, wherein the at least one slot extends along a circumference of the rotatable locking cap.

9. The apparatus of claim 1, wherein the push rod is manually actuated via a rotatable dial in communication with an actuation mechanism.

10. The apparatus of claim 9, wherein the actuation mechanism includes a spring.

11. The apparatus of claim 1, wherein the push rod includes one or more elongated ridges along a middle portion of the push rod.

12. The apparatus of claim 11, wherein a height of the middle portion is greater than a height of the distal end.

13. The apparatus of claim 1, wherein the plunger includes one or more ridges to stabilize the plunger within the plunger case.

14. The apparatus of claim 1, wherein rotating the handpiece in an amount ranging from 60 degrees to 120 degrees of rotation secures the handpiece to the IOL cartridge.

15. An apparatus for delivery of an intraocular lens (IOL), comprising:
a handpiece comprising:
a housing; and
a push rod disposed within the housing;
wherein:
a distal end of the push rod is configured to removably attach to an IOL cartridge, the IOL cartridge comprising:
a nozzle;
a compartment in fluid communication with the nozzle; and
a plunger case in fluid communication with the compartment, the plunger case comprising a protrusion and an end with a locking cap;
a plunger is disposed within the plunger case;
a portion of the plunger comprises a passage configured to receive the distal end of the push rod;
the push rod is rotatable;
the housing comprises a slot configured to receive the protrusion;
the distal end of the push rod, in a non-rotated position, has a first height, and, in a rotated position, has a second height that is greater than the first height; and
a portion of the passage of the plunger has an inner diameter that is greater than the first height.

16. The apparatus of claim 15, wherein the inner diameter is less than the second height.

17. An apparatus for delivering an intraocular lens (IOL), comprising:
an IOL cartridge comprising a nozzle and a compartment for receiving an IOL, the compartment in fluid communication with the nozzle and a plunger case, the plunger case having a protrusion and a distal end coupled to the compartment and a proximal end, and a plunger disposed within the plunger case; and
a handpiece configured to be removably coupled to the plunger case and comprising a housing including a slot configured to receive the protrusion and a push rod comprising a distal end configured to removably attach to the plunger and disposed within the housing and configured to releasably couple to the plunger of the plunger case,
wherein:
a portion of the plunger comprises a passage configured to receive the distal end of the push rod;
the push rod is rotatable;
the distal end of the push rod, in a non-rotated position, has a first height, and, in a rotated position, has a second height that is greater than the first height; and
a portion of the passage has an inner diameter that is greater than the first height.

* * * * *